United States Patent [19]

Stetman et al.

[11] Patent Number: 5,176,623
[45] Date of Patent: Jan. 5, 1993

[54] MULTIPLE FIXED ANGLE OTHOPAEDIC APPLIANCE

[75] Inventors: Joe G. Stetman, San Diego; Adriaan C. Pruyssers, Encinitas, both of Calif.

[73] Assignee: Professional Care Products Incorporated, San Diego, Calif.

[21] Appl. No.: 776,563

[22] Filed: Oct. 15, 1991

[51] Int. Cl.$^5$ .................... A61F 3/00; A61F 5/00
[52] U.S. Cl. ........................ 602/27; 602/5; 602/16; 602/23; 602/26
[58] Field of Search .............. 602/5, 16, 23, 26, 27

[56] References Cited

U.S. PATENT DOCUMENTS

| | | |
|---|---|---|
| 112,952 | 3/1871 | Niswander . |
| 130,639 | 8/1872 | Howe . |
| 552,143 | 12/1895 | Rankin . |
| 1,549,382 | 8/1925 | Riddell . |
| 2,525,658 | 10/1950 | Dumelin .................... 128/80 |
| 3,800,789 | 4/1974 | Schloss ...................... 128/90 |
| 3,955,565 | 5/1976 | Johnson ................... 128/89 R |
| 4,289,122 | 9/1981 | Mason et al. ............. 128/80 E |
| 4,340,041 | 7/1982 | Frank ....................... 128/80 C |
| 4,378,793 | 4/1983 | Mauldin et al. ........... 128/80 H |
| 4,425,721 | 1/1984 | Spronken ................... 36/11.5 |
| 4,510,927 | 4/1985 | Peters ...................... 128/80 H |
| 4,531,515 | 7/1985 | Rolfes ...................... 128/87 R |
| 4,572,169 | 2/1986 | Mauldin et al. ........... 128/80 H |
| 4,771,768 | 9/1988 | Crispen ..................... 128/88 |
| 4,890,607 | 1/1990 | Townsend ................. 128/80 C |
| 5,000,169 | 3/1991 | Swicegood et al. ........ 602/16 |
| 5,092,321 | 3/1992 | Spademan .................. 602/16 |

OTHER PUBLICATIONS

American Academy of Orthopaedic Surgeons, "Atlas of Orthotics", C. V. Mosby Co., 1985, pp. 199–209, 227, 236, 358–362.

Kent K. Wu, "Foot Orthoses", William & Wilkins, 1990, pp. 125–135.
Zinco Industries, Inc., "Controlled Ankle Motion Walker", 1990.
"ProCare", Short Leg Walker, 1990.
Support Systems, "Control Action Splint", 1980.
"ProCare", Knee Ranger Motion Control Splint, 1988–1989.

Primary Examiner—Paul Prebilic
Attorney, Agent, or Firm—Juettner Pyle & Lloyd

[57] ABSTRACT

An orthopaedic brace for articulated joints of the human body and the members of the body joined by such joints is comprised of support members for securement to respective body members on opposite sides of the joint and a hinge assembly connecting the support members and providing an axis of oscillation aligned with the axis of articulation of the joint; the hinge assembly including retention surfaces on one hinge member and a locking device on another hinge member cooperative with the retention surfaces for supporting the joint and the associated body members in any one of a plurality of fixed angle positions during normal activity; for quick release from the fixed position to a free-floating condition to enable the wearer to periodically engage the therapeutic and/or rehabilitative exercise of the joint without having to remove the brace; and for quick and facile return to the selected fixed angle position without having to engage in tedious readjustment of the brace following execise.

In the preferred embodiment illustrated and described, the appliance comprises a lower leg and ankle walker for holding the foot and ankle in any one of a plurality of fixed positions and for release from the fixed position to a free floating condition to accomodate rehabilitative afrticulation of the ankle in both dorsiflexion and plantar flexion.

22 Claims, 4 Drawing Sheets

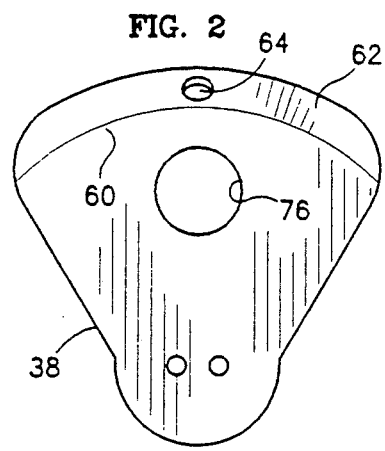
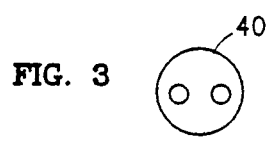
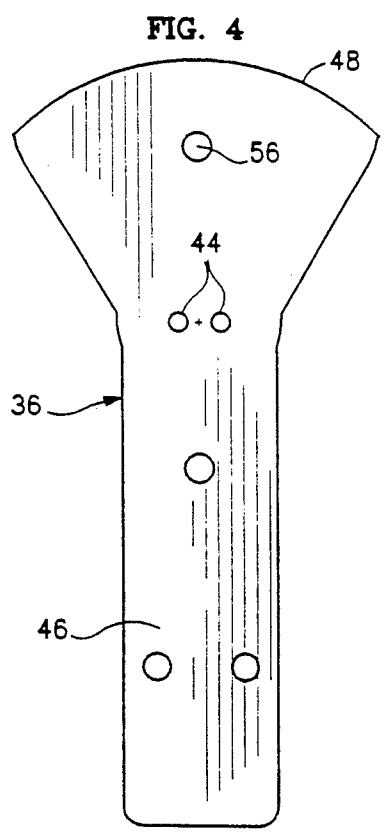
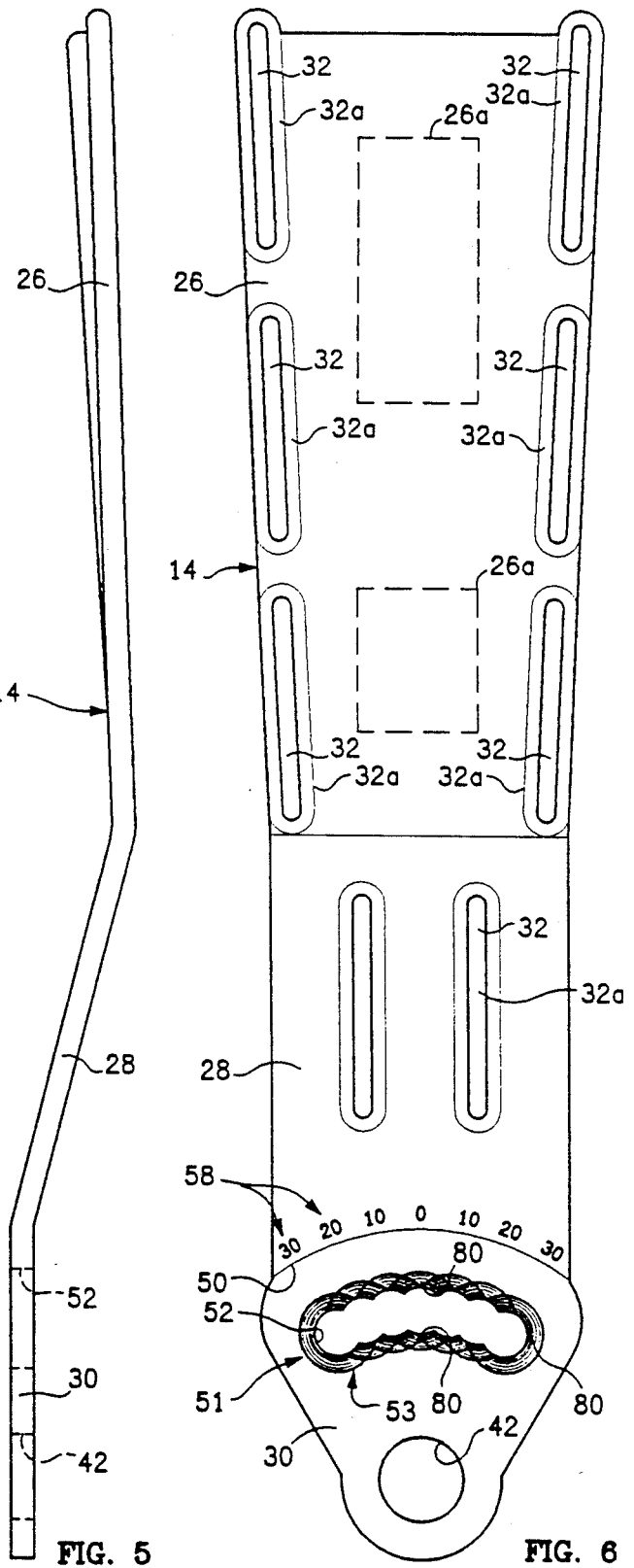

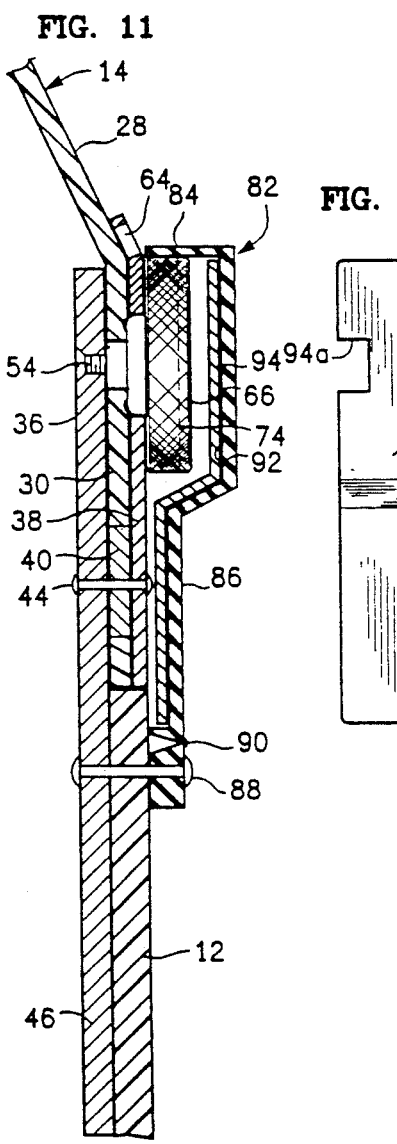
FIG. 11
FIG. 11a
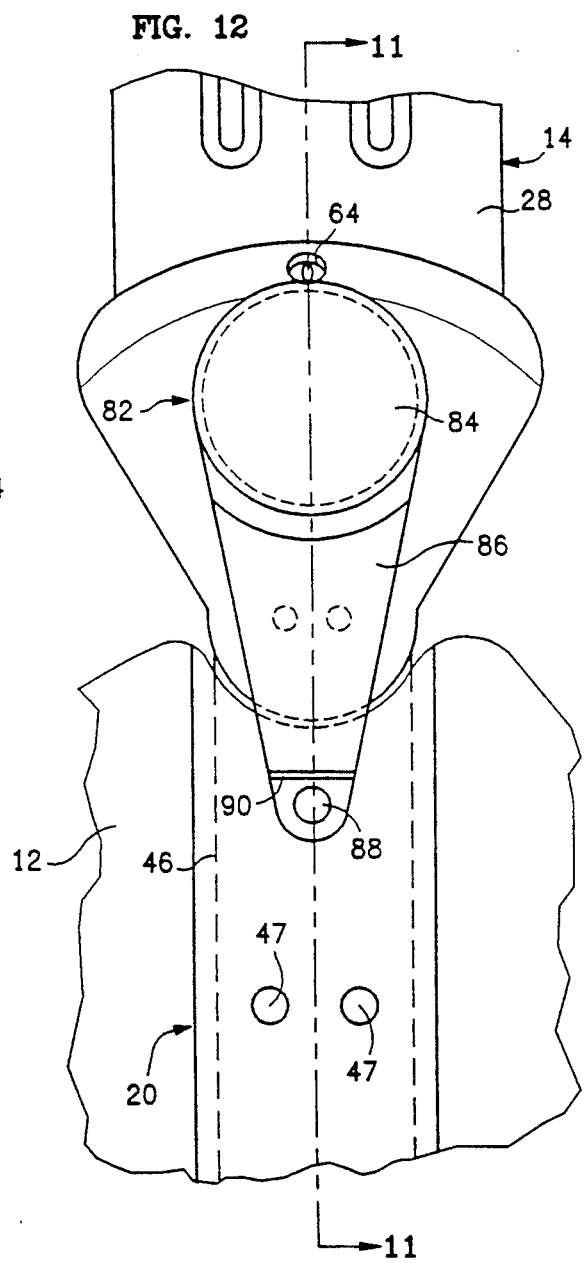
FIG. 12

MULTIPLE FIXED ANGLE ORTHOPAEDIC APPLIANCE

FIELD OF THE INVENTION

The present invention relates to orthopaedic appliances for articulated joints of the human body and the members of the body joined by such joints, most notably the elbow, hip, knee and ankle joints.

BACKGROUND OF THE INVENTION

In the treatment of injuries to articulated joints of the human body and/or the members of the body joined by such joints, particularly during the recuperation or rehabilitation period of the treatment, it is conventional in the art to fully or partially immobilize the joint and associated body members by means of a removable brace or appliance.

The prior art is replete with a wide variety of such orthopaedic appliances, including braces which retain the limb members and the joint in fixed position relative to one another, see, for example, U.S. Pat. No. 4,378,793; braces that include a joint or hinge accommodating substantially complete articulation or freedom of movement of the joint, e.g., U.S. Pat. No. 4,510,927; braces that accommodate a limited range of motion of the joint, for example, U.S. Pat. No. 1,549,382; and braces including a hinge that is adjustable to accommodate either variable limited ranges of motion of the joint and/or multiple fixed angle adjustments of the joint and the body members joined by the joint. Representative disclosures of the latter type of braces and appliances are found in U.S. Pat. No(s). 4,340,041, 4,531,515 and 4,771,768.

Frank U.S. Pat. No. 4,340,041 is directed to a knee brace including a hinge comprising a pair of semi-circular plates secured to opposite sides of a rigid anchor bar, and a second anchor bar inserted between the two plates and pivotally connected to the plates by a central pivot pin. The two semicircular plates are provided with corresponding pairs of holes formed concentrically about the pivot axis, and the second bar contains holes which are adapted to be aligned with a corresponding pair of the holes in the two plates. A securing bolt is adapted to be inserted through a hole in one of the plates through one or the other of the holes in the second bar, and threaded into the corresponding hole in the other of the plates, thereby to lock the second bar in any one of a multiple of fixed angle positions relative to the first bar. However, in order to adjust the angle between the bars or to release the hinge, it is necessary to completely remove the bolts from two hinges, one each on the opposite sides of the knee, and then subsequently to realign the bolt holes in the proper locations on both sides of the knee and to replace the bolts which, assuming the bolts have not been misplaced, is neither easy nor convenient to accomplish.

Rolfes U.S. Pat. No. 4,531,515 discloses a hip and upper leg brace including a hinge arrangement similar to that of Frank wherein a pair of pins can be so arranged in a circular yoke as to lock two support arms in anyone of a multiple of fixed angles relative to one another, or to permit various ranges of motion between the two arms. The Rolfes hinge suffers essentially the same disadvantages as the Frank hinge.

Crispin U.S. Pat. No. 4,771,768 is directed to a lower leg and ankle brace or walker including a very complex and difficult to adjust ankle joint hinge having four individually adjustable control members that are adapted to be adjusted to various fixed angles and that can also be adjusted to selectively allow articulation through controlled angular ranges of motion within preset limits in dorsiflexion only, in plantar flexion only, or in combined dorsiflexion and plantar flexion. The hinge structure is far more complex than required by the art, and is extremely difficult to adjust.

SUMMARY OF THE INVENTION

The object of the present invention is to provide an improved orthopaedic brace for articulated joints of the human body and the members of the body joined by such joints.

In particular, it is an object of the invention to provide an improved articulated brace that provides for support of an articulated joint and associated limb members in any one of a plurality of fixed angular positions during normal ambulatory activities; for quick release from the fixed position to a free floating condition to enable the wearer to periodically engage in therapeutic or rehabilitative exercise of the joint without having to remove the brace; and for quick and facile return of the brace to the selected fixed angle position without having to engage in tedious readjustment of the brace following exercise.

For many of the injuries that are imparted to elbows, hips, knees and ankles and adjacent portions of the associated limbs, a single, preselected fixed angle of repose of the joint and limbs, selected by the treating physician or therapist for use during the course of rehabilitation, is the indicated or proper treatment for the injury. For such injuries, a limited range of motion is neither necessary nor desired, and complication of the brace and its hinge to accommodate a range of motion is wasteful; both economically and with regard to the time and patience of both the care provider and the patient. The ability to adjust the brace to any one of a number of fixed angles that may be desired by the care provider is of primary concern.

Another factor of primary concern relates to periodic therapeutic or rehabilitative exercise by the patient of the afflicted or affected joint. Basically, what is desired is the ability to release the brace from its fixed position, without removing the brace from or changing its orientation relative to the joint and the associated limbs, so that the patient can flex or move the joint and limbs, by dorsiflexion and plantar flexion of the foot in the case of the ankle, and by flexion and extension of the lower leg or lower arm in the case of the knee or elbow. If this can be accomplished without having to remove the brace, the brace will serve to hold the joint and associated limbs in proper orientation one to another to ensure against further traumatization in the course of rehabilitative exercise.

Finally, the hinge or hinges of the brace should accommodate fast and easy release of the brace from its preselected fixed position to a free floating exercise position, and fast and easy return of the brace to said preselected fixed position.

It is the object of the invention to provide an improved articulated brace that meets all of these highly desirable criteria, and does so in an economical and facile manner.

These and other objects and advantages of the invention will become apparent from the following detailed description, as considered in connection with the accompanying drawings.

BRIEF DESCRIPTION OF THE DRAWINGS

FIGS. 2, 3 and 4 are front elevations of respective piece parts of a hinge subassembly intended to be affixed to the shoe portion of the walker illustrated in FIG. 1;

FIGS. 5 and 6 are, respectively, a side elevation and a front elevation of a component intended to comprise the leg support portion of the walker illustrated in FIG. 1;

FIG. 11 is a vertical section of a modification of the hinge illustrated in FIG. 7;

FIG. 11a is a front elevation of a tool or wrench that may be incorporated in the modification of FIG. 11; and FIG. 12 is a front elevation of the modified hinge of FIG. 11.

DETAILED DESCRIPTION

The following is a description of the best mode presently contemplated by the inventors for carrying out their invention. The invention was conceived and reduced to practice during the course of development of an orthopaedic lower leg and ankle walker, and the drawings and description therefore illustrate and describe such walker. However, as the description proceeds, persons of reasonable skill in the art will readily perceive the applicability, and the manner or mode of application, of the principles of the invention to other articulated joints of the body, e.g., the hip, knee and elbow.

Figure 1:
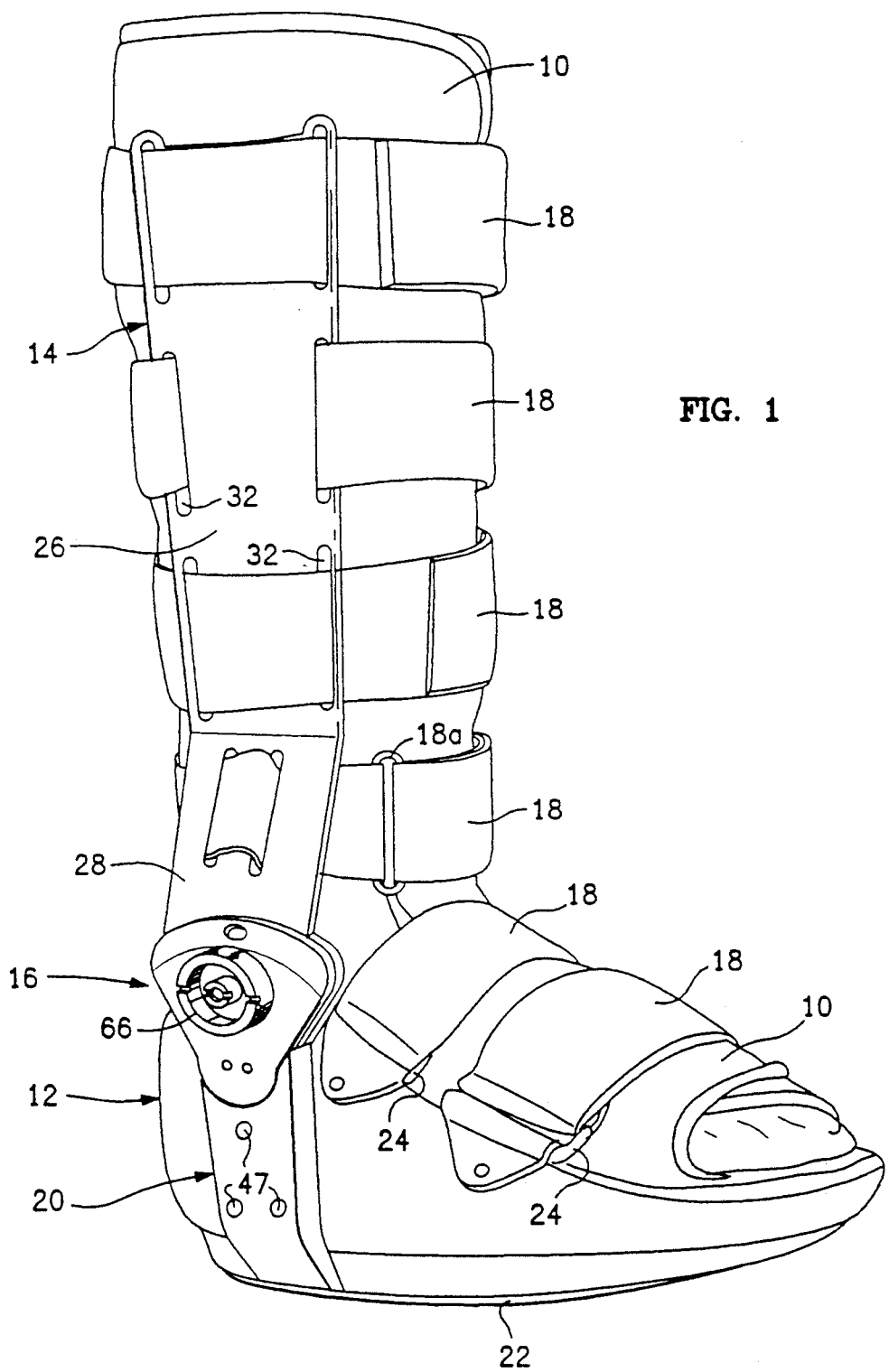
FIG. 1 is a perspective view of an orthopaedic walker provided in accordance with the present invention for use in the recuperative treatment of lower leg, ankle, heel and foot injuries.
Figure 7:
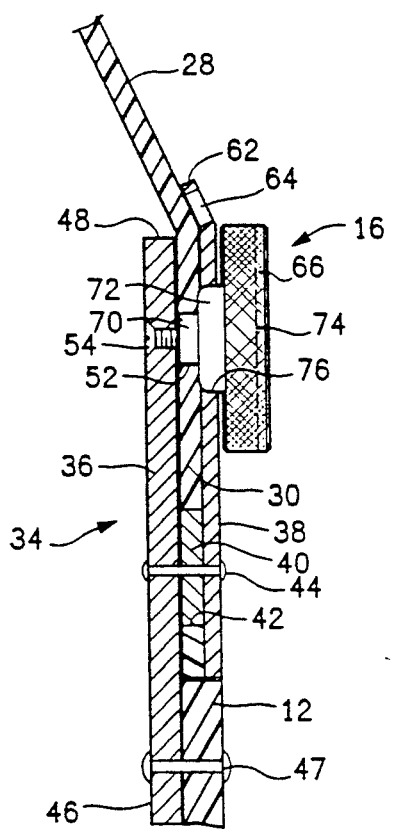
FIG. 7 is a vertical section and FIG. 8 is a front elevation of the preferred embodiment of a multiple fixed angle hinge for the walker illustrated in FIG. 1.

Referring to FIG. 1, the preferred embodiment of the improved orthopaedic walker is illustrated as being comprised of a preformed lower leg, ankle and foot pad and wrapper 10 adapted to be wrapped about the lower leg, ankle and foot of the patient and to serve as a cushion between the leg, ankle and foot and the orthopaedic appliance; a rigid shoe 12 to receive and support the foot of the patient; a pair of lower leg supports or arms 14 on opposite sides of the patient's lower leg (only one of which is visible in FIG. 1); a pair of hinges or hinge assemblies 16 (only one of which is visible) pivotally connecting the lower ends of respective ones of the leg supports 14 to the opposite sides of the shoe at the level of the ankle; and a plurality of adjustable straps 18 for adjustably and releasably securing the walker to the lower leg and foot of the patient.

The pad or wrapper 10 is conventional in the art and is comprised of a polymeric foam cushioning material having a plush or pile exterior surface receptive of the hook members of fabric hook and pile fastening means, such as those sold under the trademark "Velcro". The polymeric foam is preferably preformed to conform to and mate with the posterior of the lower leg and the heel and sole of the foot of the patient, and includes opposed flap portions to be wrapped around the anterior surface of the lower leg and the side and upper surfaces of the ankle and the foot. If desired, the inner surface of the exterior or overlying one of the flaps may include hook type fabric fastening means for engagement with the exterior pile surface of the underlying flap to adjustably secure the wrapper about the foot, ankle and lower leg.

The shoe 12 comprises a rigid open top shell, suitably molded from a polymeric resin, having a bottom wall, side walls and a heel, but no top or upper. Adjacent the heel, the side walls each extend upwardly to adjacent the malleolus of the patient's ankle and each has a semicircular cut-out in the top edge generally conformed to the lower margin of the malleolus. At this point, i.e., from the malleolus down to the sole, each side wall of the shoe is bulged outwardly, as indicated at 20, to form an internal vertical recess for reception of one of the support members or arms of the respective one of the hinges 16. The bottom or sole of the shoe is curved continuously from the heel to the toe to complement the gait of the patient and is covered with a nonslip rubber or composition sole 22 for purposes of safety in walking.

Two of the flexible straps 18 are secured at one end, suitably by means of rivets (not shown) to one of the sidewalls of the shoe, passed over the top of the patient's foot, threaded through buckles 24 riveted or otherwise secured to the other sidewall of the shoe, and folded back on themselves for securement over the foot by conventional hook and pile fastening means. If desired, hook fastener means may also be adhered to the inner surface of the sole of the shoe for engagement with the exterior pile surface of the padding 10 at the sole of the foot to prevent relative movement between the shoe, the padding and the patient's foot.

The leg supports 14, only one of which is illustrated, each comprise, as best shown in FIGS. 5 and 6, an upper portion 26 that is curved transversely to complement the leg of the wearer and extends from slightly below the knee of the patient downwardly toward the patient's ankle. From a location above the ankle, the support is inclined downwardly and outwardly away from the leg, as indicated at 28, and then extends vertically downwardly outwardly of the ankle, as indicated at 30, to a location aligned with the malleolus and the axis of articulation of the patient's ankle. The lower vertical end portion 30 of the support 14 comprises one element of the hinge 16, presently to be described. As will be observed from FIG. 6, the support 14 is symmetrical and will fit against and complement either side of either leg of the patient. Consequently, the two leg supports 14 of the brace will be identical, with one support engaging the inner or medial surface of the leg and the other support engaging the outer or lateral surface of the leg.

Each support 14 is provided with loopholes 32 in the leg engaging and inclined portions 26 and 28 thereof for reception and passage therethrough of respective ones of the straps 18, with one strap encircling the leg just above the ankle and with three vertically spaced straps encircling the lower leg of the patient between the ankle and the knee, to firmly secure the brace to the patient's leg.

The strap passing through the loops in the inclined portions 28 of the leg supports encircles the leg just above the patient's ankle and aids, when the brace is in a fixed position, in immobilizing the ankle. One end of this strap includes a buckle 18a through which the other end of the strap is threaded and folded back on itself, so a precise degree of tension can be applied to the brace at this location.

The three straps 18 above the ankle encircle the leg in opposite directions one to another to mitigate twisting and/or shifting of the leg supports during ambulatory movement of the leg by the patient.

The inner surfaces of the upper portion 26 of each of the two leg supports is also provided with one or more strips of hook fastening means, indicated at 26a in FIG. 6, lockingly engageable with the pile surface of the pad 10, whereby to maintain a fixed relationship therebetween so that once a brace is fitted to a patient it need not be fitted again, even if the brace is temporarily removed for bathing or other hygenic or therapeutic purposes.

It is a particular feature of the invention to form each leg support 14 as a unitary molded plastic element to facilitate economical mass production of a combined leg support and hinge member of complex configuration. Unitary molding also facilitates the provision of reinforcing bosses 32a about each of the loop holes 32, and the provision of a leg supporting member that affords firm, rigid support, yet is lightweight and economical.

As noted above, the lower end portion 30 of each leg support 14 forms one arm or hinge plate element of each of the hinge assemblies 16 of the invention. The other arm or support element of each hinge, indicated generally at 34, is comprised of an inner or main plate or support member 36 (FIG. 4), an outer guide plate 38 (FIG. 2) to be secured to the plate 36, and a bearing 40 (FIG. 3) to be inserted between the two plates to space them apart. When assembled, the support and guide members 34 and 36 define a fork or yoke for reception of the hinge element 30 and the bearing 40 defines a pivot on which the upper hinge plate 30 is journaled for rotation, i.e., oscillation, relative to the lower hinge element 34.

The bearing 40 is of relatively large diameter and the element 30 is provided adjacent its lower end with a complementary relatively large diameter hole 42 for conformable reception of the bearing, thereby to define a low friction, long wearing bearing assembly. The bearing 40 may if desired be formed of a low friction plastic, such as Delrin, or any other suitable material.

To effect assembly of the hinge, two rivets 44 are passed through respective pairs of holes in the plate 36 and the bearing 40; the upper hinge plate 30 is then journaled on the bearing by means of the hole 42; the guide plate 38 is aligned with plate 36 and slipped over the rivets 44; and the rivets are peened or expanded at their outer ends to hold the four components 30, 36, 38 and 40 together in assembled relationship. The two rivets 44 secure the plates 36 and 38 against relative rotation and hold the two plates and the bearing 40 together in fixed relationship to form the lower hinge element 34, and the bearing 40 mounts the upper hinge element 30 between the plates 36 and 38 for rotary or oscillatory movement relative to such lower hinge element 34.

The main plate or support member 36 of each hinge element 34 includes a downwardly extending shank 46 of a length and width corresponding to the length and width of the vertical recess defined by the lateral bulge 20 on the respective side of the shoe; and the shank is inserted within said recess and fixedly secured to the respective side wall of the shoe by a plurality of rivets 47 (FIG. 1). The shoe 12 is thus secured to the two lower hinge elements 34 and is thereby pivotally mounted to the lower ends of the support arms 14 for oscillation about an axis which is defined by the centers of the bearings 40 of the two hinge assemblies 16, one on each side of the ankle. The centers of the two bearings are preferably coaxial and define a single common pivot axis aligned with the axis of articulation of the patient's ankle.

Upwardly from the pivot axis defined by the bearings 40, the plates 36 and 38 and the upper hinge element 30 flare outwardly, i.e., forwardly and rearwardly relative to the ankle, essentially along symmetrical borderlines parallel to corresponding symmetrical radii of the bearing axis. In the case of an ankle brace or walker, maintenance of symmetry results in a universal hinge structure, that is, a hinge that may be used universally on either side of either ankle, i.e., on either of the left and right hand sides and either of the medial and lateral sides of either of the ankles. As a consequence, only one model of hinge is required, rather than separate right and left handed hinges and/or separate medial and lateral hinges.

In addition, by appropriate formation of the shoe 12 for application to both the right foot and the left foot, there is no need for right and left foot versions of the improved brace, and only a few sizes of shoes and leg supports need by provided, e.g., juvenile, medium and large, thereby to achieve economies in production, warehousing, etc.

The main plate 36 of the lower hinge element and the vertical plate portion 30 defining the upper hinge element terminate at their upper edges on respective arcs 48 and 50 which are substantially concentric with the axis of oscillation between the two hinge members, i.e., with the axis of the bearing 40. The arcuate edges 48 and 50 are formed on essentially the same radius of curvature as one another and are essentially coextensive with one another. Adjacent to and substantially concentric with its upper edge, the hinge plate 30 is provided with retention means or surfaces 51 in the form of an arc substantially concentric with the axis of oscillation between the hinge members 30 and 36. The retention means 51 preferably comprises a plurality of angularly or arcuately spaced recesses 53, and in the preferred embodiment, the recesses extend through the hinge plate 30 and overlap one another so as to define an arcuate slot 52 comprised of a plurality of angularly spaced steps, notches or holes. In the preferred embodiment, the arcuate slot 52 accommodates passage therethrough of a suitable means for limiting or restricting relative movement between the hinge elements 30 and 34. As shown, such means preferably comprises a threaded screw, bolt or stud 54 of a diameter smaller than the minimum width dimension of the slot that is passed through and preferably secured within a hole 56 in the plate 36 and that extends into the slot 52 in axial alignment with the arcuate center line of the slot.

Figure 8:
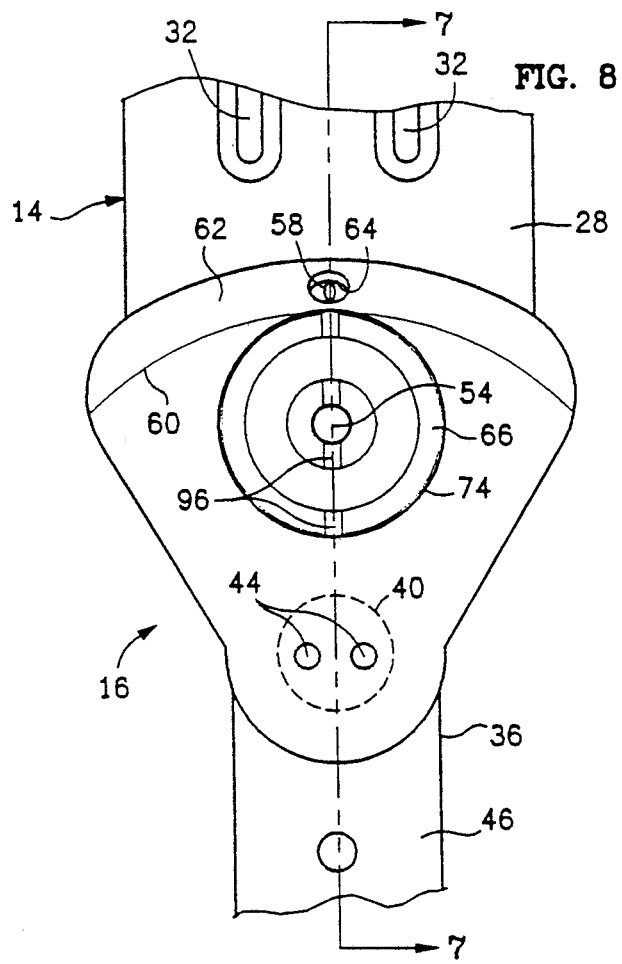

In the embodiment of the hinge preferred for ankle braces, and with the stud 54 extending into the slot 52, the slot is formed of sufficient arcuate extent relative to the stud to accommodate sixty degrees of relative rotation or oscillation of one hinge element relative to the other, specifically, a symmetrical thirty degrees to each side of a zero or central position wherein the shank 46 of the hinge element 36 is aligned vertically with the associated leg support or upright 14, as illustrated in FIGS. 1 and 8. To facilitate setting the hinge in specific angles of adjustment of one hinge element relative to the other, the recesses 53 defining the retention means 51, i.e., the steps or notches in the slot 52, are so spaced as to define seven circular or partly circular recesses or holes formed respectively on centers located ten degrees apart on the arcuate center line of the slot 52, one at the center of the arc and three on each side of center located respectively at 10, 20 and 30 degrees from the center. The respective recesses for the various angles of adjustment may appropriately be designated on the upper hinge element 30 by indicia or markings 58 indicating the respective angles of adjustment, as shown for example in FIG. 6.

In the preferred embodiment shown in FIG. 6, the indicia or markings 58 are provided on the inclined portion 28 of the upper hinge element just above the arc 50 defining the upper edge of the vertical portion 30. Such markings are preferably integrally molded onto or into the element during plastic molding of the leg support. By locating the angle markings or indicia on the inclined portion 28, enhanced visibility of the markings is afforded to both the care provider and the patient for ease and facility in setting the brace in or returning the same to a desired fixed angle of adjustment.

The outer guide plate 38 of the lower hinge element has the same shape or configuration as the upper extremity of the main plate 36, including an arcuate formation at 60 that is essentially coincident with the arcs 48 and 50 at the upper edges of the plates 36 and 30. In addition, the plate 38 includes an upwardly extending and inwardly inclined arcuate top portion 62 which overlies the lower margin of the inclined portion 28 bearing the angle of adjustment markings 58. To accommodate viewing of the markings, the inclined portion 62 is provided with a window, for example, a hole or slot 64, of a size to reveal one marking at a time, and only one at a time, thereby to facilitate precise adjustable setting of the hinge without variation from the desired setting. Due to the inclination of the top edge portion 62 of the plate 38 and the location of the angle markings 58 on the inclined surface 28 of the support 14, the angle markings are readily visible through the window 64 to the person wearing the brace, as well as the care provider fitting the brace. If desired, a vertical slot extending through the top edge of the inclined portion 62 could be provided in lieu of the illustrated hole 64 to increase or enhance the visibility of the markings to the wearer of the appliance as the wearer looks downwardly onto the hinges 16 on the opposite sides of the leg.

To lock the hinges in a selected fixed angle of adjustment, each hinge is provided with locking means associated with and adjustably mounted on a hinge plate other than the hinge plate bearing the retention means 51 for selective cooperative engagement with and disengagement from the retention means. In the preferred embodiment, each hinge includes a locking member in the form of a nut or knob 66 having a threaded bore 68 for threaded engagement with the bolt or stud 54 that extends into the respective arcuate adjusting slot 52. Each nut or knob 66 also has a stem 70 of a diameter to fit conformably within the arcuate slot 52, a cam portion 72 of a diameter larger than the maximum width (radially thereof) of the arcuate slot 52 adapted for locking engagement with the retention means, i.e., with the surface portions of the hinge plate 30 adjoining the marginal edges of the recesses 53, and a circular handgrip 74 of enlarged diameter facilitating manual rotation and consequent adjustment of the knob on the stud 54 inwardly and outwardly relative to the hinge plate 30. The peripheral surface of the hand grip 74 is preferably knurled to facilitate nonslip grasping of the same. To accommodate passage of the cam 72 for engagement with the element 30, the guide plate 38 is provided with a hole 76 of slightly larger diameter than the cam and aligned axially with the bolt 54.

In prior art devices, it has been customary to utilize removable bolts or pins to provide for various fixed angle positions of adjustment and/or various limited ranges of motion of the hinge of an orthopaedic brace. Upon removal, such bolts or pins are easily lost or misplaced, and even if not lost, replacement of the same in the proper location in the hinge to attain the desired angle of adjustment is neither easy nor convenient to accomplish. In accordance with the present invention, the locking member or nut 66 is not removed and remains associated with the stud 54 and hinge plate 36 at all times, particularly when the nut is loosened sufficiently to accommodate free floating oscillatory movement of the upper and lower hinge elements. To this end, the stud 54 is of sufficient length that the nut 66 may be backed completely away from the hinge plate 30 without becoming disassociated from the stud 54. Moreover, it is preferred that the locking means be permanently associated with the hinge plate on which it is mounted, or at least not removable therefrom in normal use, thereby to prohibit loss or misplacement of the locking means. For the purpose, the threaded stud 54 and the threaded portion 68 of the nut 66 are of such lengths relative to one another that the outer end of the stud protrudes outwardly slightly beyond the outer end of the thread 68 when the nut is backed completely away from the hinge plate 30, and interference is established between the outer ends of the stud 54 and the thread 68 to prohibit removal of the nut from the stud. Specifically, with reference to FIG. 10 which shows the hinge plate 30, the stud 54 and the nut 66 prior to assembly of the nut on the stud, the nut 66 is threaded onto the stud until the outer end of the stud protrudes beyond the outer end of the thread 68, whereafter the outer end of the stud is staked, i.e., radially expanded, so that the nut cannot thereafter be removed from the stud by normal hand rotation of the nut. Thus, the locking means 66 will remain associated with the hinge plate 36 on which it is mounted in all positions and during all modes of operation of the hinge.

To insure that the stud 54 does not protrude beyond the nut 66 and create a potentially dangerous sharp protrusion at the exterior of the brace, the nut is of a sufficiently long axial dimension and is counterbored outwardly of the thread 68 to receive and house the outer end of the stud in all positions of adjustment of the nut on the stud.

When the nut or knob 66 is loosened, i.e., backed off away from the plate 30 on the stud 54, the upper and lower hinge elements 30 and 34 are freed for oscillation relative to one another about the axis of the bearing 40 through the arc of movement accommodated by the slot 52, i.e., 60 degrees in the illustrated embodiment. If the stem 70 is formed of a diameter less than the minimum width dimension of the slot 52, the knob 66 need only be loosened sufficiently for the cam 72 to clear the upper hinge plate 30. If the stem 70 is of a diameter intermediate the minimum and maximum width dimensions of the slot 52, e.g., of a diameter nearly the same as that of the recesses, i.e., the notches or steps in the slot, it will be necessary to back the nut 66 off a distance sufficient for the stem 70 to clear the hinge plate 30. The latter arrangement affords the advantage that the stem 70 fits within each one of the steps, notches or holes and thereby provides for alignment, or at least initial or preliminary alignment, of the nut 66 relative to the selected recess, notch or hole, and also assists in maintaining the nut against relative angular displacement from the selected notch or hole. The preliminary alignment function may be enhanced by imparting a modest taper to the exterior surface of the stem 70.

Figure 9:
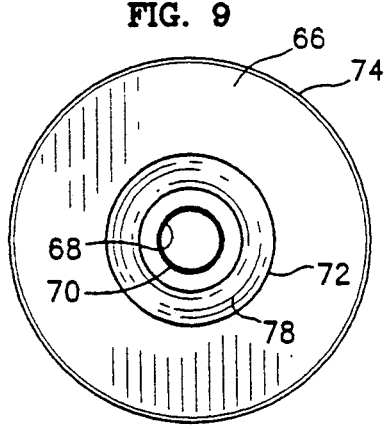
FIG. 9 is a rear elevation of an angle selection and securing knob for the preferred embodiment of the hinge illustrated in FIGS. 7 and 8.
Figure 10:
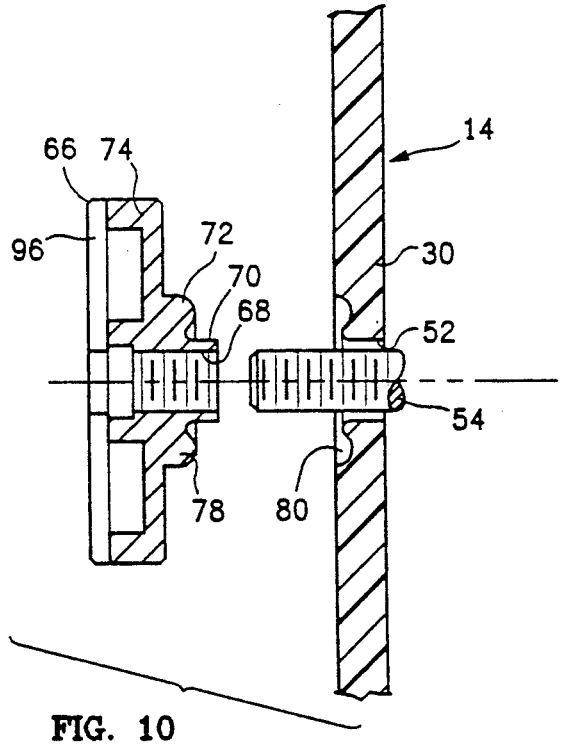
FIG. 10 is a vertical section, on an enlarged scale, of the components (prior to assembly) of the angle selection and securing means for the preferred embodiment of the hinge illustrated in FIGS. 7 and 8.

To assure retention of the hinge elements in a selected fixed angular relationship, particularly when the hinge element 30 is formed of plastic as is preferred, the surface of cam 72 facing toward the element 30 and the juxtaposed surfaces of the element 30 adjoining the marginal edges of the recesses 53 are provided with complementary interengaging surfaces. Specifically, as shown in FIGS. 9 and 10 (see also FIG. 6), the annular surface or shoulder 78 defined between the stem 70 and the periphery of cam 72, which faces toward the plate or element 30, is of toroid form (i.e., like one surface of a doughnut) and each of the seven recesses, steps or notches 53 is surrounded, to the extent possible, by complementary toroidal shaped recesses 80 formed in the juxtaposed surfaces of the plate 30. Consequently, as the nut or knob 66 is tightened down on the stud 54, the stem 70 enters the selected hole or notch in the slot 52 and preliminarily aligns the cam 72 axially relative to the hole. As tightening continues, the toroidal surface on the shoulder of the cam enters into the toroidal recesses surrounding the selected hole, whereupon the complementary toroidal surfaces guide the nut 66 into perfect alignment within the selected hole. Further tightening causes the toroidal surfaces to become firmly frictionally engaged with one another to securely lock the hinge and the hinge elements or arms 30 and 34 in the selected angular relationship. Utilizing a metal nut 66 with a plastic upright or arm 30, the plastic member may be elastically deformed to a degree to assist in retaining the hinge elements in fixed angular relationship.

The walker illustrated in FIG. 1 may therefore be adjusted so that the shoe 12 is normal to the leg supports or uprights 14, or may be adjusted to various fixed angles in either dorsiflexion or plantar flexion, specifically, any of 10, 20 or 30 degrees in plantar flexion (with the toe of the shoe moved downwardly away from the leg) and either 10 or 20 degrees in dorsiflexion (with the toe of the shoe moved upwardly toward the leg). While the preferred embodiment of the hinge, due to its universal adaptability, will accommodate 30 degrees of dorsiflexion, fixation of the foot in such extreme degree of dorsiflexion would not frequently be recommended or utilized by a doctor or physical therapist.

In use of the walker, with the walker secured to one leg and foot of the patient in the manner indicated in FIG. 1, and assuming the two hinges 16, one on each side of the encased ankle, are fixed or locked in a position of 10 degrees of dorsiflexion, the patient may engage in as much ambulatory movement as the patient desires and the walker will retain the lower leg, ankle and foot of the patient essentially rigidly in the fixed position deemed by the care provider to be the most beneficial for recuperation and rehabilitation of the injury suffered by the patient.

When at rest, and dependent upon the instructions of the care provider, the patient may exercise the ankle joint, for relaxation and/or for therapeutic purposes, simply by loosening the two locking nuts 66 to render the hinges 16 free floating. The patient may then oscillate his/her foot up and down, in dorsiflexion and/or plantar flexion, through any desired arc of movement up to 60 degrees, while the components of the brace retain the leg, foot and ankle in proper orientation one to another to prevent further traumatization.

Upon completion of the exercise, the patient simply moves her/his foot back toward the selected angle, in this example 10 degrees of dorsiflexion, until the numeral "10" appears in the windows 64 in the hinges 16, whereupon the patient may tighten down the nuts 66 to firmly lock the brace in the specified fixed angle of adjustment. Due to the guiding and camming actions provided by the stem 70, the cam 72 and the complementary toroidal surfaces 78 and 80 in each hinge, the patient need not be concerned with aligning the numeral "10" precisely in the respective window, since precise alignment will be achieved by the guiding and camming surfaces as the respective locking nuts are tightened down. The patient can be assured of proper adjustment simply by checking whether the numeral "10" appears clearly in each window 64 following tightening of the nuts.

The walker of the invention and its associated hinges therefore provide for fast and easy adjustment of the walker to any of a plurality of fixed angle positions of the foot and leg, quick release from the fixed angle to free floating condition for rehabilitative exercise, and fast and easy return of the walker to the selected fixed angle of adjustment for safe and proper ambulatory activity.

The walker further accommodates and facilitates hygienic attention to the patient's leg, foot and ankle, e.g., for bathing, by the simple expedient of opening the six straps 18 illustrated in FIG. 1 and removing the brace. When removed from the patient's leg and foot, the brace and its components remain in the same orientation relative to one another as first adjusted by the doctor or therapist, since the padded wrap 10 is preformed to fit the leg, ankle and foot, the shoe 12 and the leg supports 14 are attached to the wrap, and the straps 18 are affixed respectively either to the shoe 12 or to both of the leg supports 14. Consequently, when the patient's foot, ankle and lower leg are reinserted into the brace, the foot, ankle and leg will all reassume their preset orientation with the brace, and all that need be done is redo the straps 18.

Thus the walker of the invention equips the care provider and the patient with a highly advantageous appliance for use in facilitating recuperative and rehabilitative treatment of an injured leg, ankle or foot.

In particular, the improved hinge provided by the invention is not complex or complicated, and is very easy to use, especially in relation to relevant prior art hinges. Also, the brace is readily and economically produced, particularly when the leg supports or uprights 14 and their associated hinge components 30, 42, 52, 58 and 80 are directly molded from plastic as a unitary finished product not requiring machining.

Referring now to FIGS. 11 and 12, a modified embodiment of the hinge is illustrated as including a decorative and protective shield 82 for the fastening nut 66, which shield also accommodates a tool or wrench (FIG. 11a) facilitating tightening and loosening of the nut. The hinge itself is of the same construction as that illustrated and described in connection with FIGS.

7-10, and corresponding reference numerals are employed in FIGS. 11 and 12 to designate corresponding components.

The shield 82 is conveniently formed as an integral plastic molding having an upper, circular, cup-shaped portion 84 of an inner diameter essentially equal to or slightly smaller than the outer diameter of the hand grip portion 74 of the nut 66 and adapted to have a snug, press fit onto the periphery of the hand grip 74. An integral mounting leg 86 extends radially downward from the cup shaped portion and is affixed at its lower end, by a rivet 88 or the like, to the sidewall of the shoe 12 and/or the shank 46 of the hinge piece 36. The mounting leg 86 thus premanently associates the shield with the hinge and prevents rotation of the shield about the axis of the nut 66. A lateral hinge 90 is integrally molded into the leg 86 just above the rivet 88 so that the portions of the shield above the hinge 90 may be swung away from the brace to a horizontal, out of the way location, to accommodate freedom of access to the nut 66.

The internal peripheral wall of the cup shaped portion 84 has a press fit onto the peripheral surface of the hand grip 74 and serves, in conjunction with the knurled surface of the hand grip, to aid in preventing inadvertent rotation and consequent tightening or loosening of the nut 66. Also, the shield covers the nut or knob 66 to prevent harm to the patient and to objects the patient might bump into, e.g., the patient's other leg, friends' legs, furniture, etc.

Within its interior surface, the shield 82 has an elongate rectangular recess 92 which houses a tool or wrench 94 adapted for use in tightening and/or loosening the nut 66. The wrench 94 is simply a flat piece of metal, bent between its ends to conform to the internal configuration of the shield 82, and adapted to be used edgewise for engagement with the nut. For the purpose, the outer facial surfaces of the nut 66 are provided with recesses, as shown in FIGS. 8 and 10, defining a diametric slot or groove 96 of a width to receive the edge of the tool, specifically, the upper left hand edge portion of the tool as it is illustrated in FIG. 11a. This edge of the tool has a cut-out 94a therein to ensure against interference between the tool and the nut retaining threaded stud 54 when the tool is inserted edgewise into the slot 96.

When the patient or care provider desires to secure the hinge in a selected fixed position or to release the hinge of the walker from the selected fixed angle position, for example, for purposes of exercise, the cup portion of the shield is swung outwardly away from the nut to a horizontal position defined by the shield hinge 90, thereby accommodating freedom of access to the hand grip 74. If the nut is too tight to be conveniently released by hand, the tool is removed from the interior of the shield and inserted edgewise into the slot 96 in the nut 66 to provide a radial lever arm facilitating release of the nut from its locked position. The tool may also be used to tighten the nut, which is particularly beneficial when the patient is relatively weak or frail. Following use, the tool 94 is returned to the recess 92 and the cup or cap 84 is pressed back onto the nut to fulfill its decorative and protective functions.

The invention has therefore been shown to provide an improved orthopaedic appliance that can quickly be adjusted to any one of a number of fixed angular positions, that can quickly and easily be released from the fixed position to a free floating condition to accommodate rehabilitative exercise, and that can quickly and easily be returned to the preselected fixed angle position. The objects and advantages of the invention have therefore been shown to be attained in a facile and economical manner.

While a preferred embodiment of the invention has been herein illustrated and described, it is to be appreciated that various changes, rearrangements and modifications may be made therein without departing from the scope of the invention, as defined in the appended claims.

What is claimed is:

1. An orthopaedic lower leg and ankle walker for supporting the lower leg, ankle and foot of a patient, comprising a shoe for reception of the foot of the patient, said shoe including upwardly extending lateral and medial sidewall portions each terminating below the malleolus of the ankle of the patient, of said shoe extending upwardly respectively from of said shoe extending upwardly respectively from respective ones of said sidewall portions outwardly of the malleolus on respective sides of the patient's ankle, a pair of lower leg support members extending upwardly respectively from the malleolus on the respective sides of the patient's ankle along the respective sides of the patient's leg, a pair of second hinge members located respectively at the lower ends of respective ones of said leg support members, means connecting the second hinge member on each side of the patient's ankle to the first hinge member on the same side of the patient's ankle for oscillatory movement about an axis substantially aligned with the axis of articulation of the patient's ankle, second hinge members on at least one of said first and second hinge members on at least one side of the patient's ankle including retention means in the form of an arc substantially concentric with the axis of oscillation between said hinge members on said one side of the ankle, locking means associated with and adjustably mounted on the other one of said first and second hinge members on said at least one side of the patient's ankle in alignment with said retention means, said locking means being selectively engageable with said retention means and including at least one surface portion lockingly engageable with said retention means, said retention means and locking means being so arranged relative to one another that said locking means is aligned with a mid-portion of the arc of said retention means when said shoe is generally perpendicular to said leg support members, said locking means being adjustable to engage said surface thereof with said retention means for selectively locking said hinge members together in said position wherein said shoe is perpendicular to said leg support members and in any of a plurality of positions in dorsiflexion and plantar flexion of said shoe relative to said leg support members within the limits of the arc of said retention means, and to be disengaged from said retention means while remaining associated with said other hinge member to accommodate free floating oscillatory movement of said shoe relative to said leg support members in both dorsiflexion and plantar flexion, whereby said hinge members may be locked in any of a plurality of selected positions of adjustment, quickly released from such position to accommodate rehabilitative exercise of the patient's ankle in plantar flexion and dorsiflexion, and quickly returned to and locked in the selected position of adjustment, and means for releasably securing said shoe to the patient's foot and said leg support members to the opposite sides of the patient's leg.

2. An orthopaedic walker as set forth in claim 1 wherein said retention means comprises a plurality of angularly spaced recesses and said surface on said locking means is selectively engageable with portions of said one hinge member adjoining the margins of each said recess for selectively locking said hinge members in any one of the angular positions defined by said recesses.

3. An orthopaedic walker as set forth in claim 2 wherein said recesses extend through said one hinge member and overlap one another to define an arcuate slot comprised of a plurality of angularly spaced notches, and wherein said locking means extends into said slot and said surface portion on said locking means is selectively engageable with surface portions on said one hinge member adjoining the marginal edges of each of said notches for selectively locking said hinge members in any one of the angular positions defined by said notches.

4. An orthopaedic walker as set forth in claim 2 wherein said locking means includes a cam portion having a toroidal surface facing toward and engageable with juxtaposed surface portions on sad one hinge member, and said juxtaposed surface portions on said one hinge member include complementary toroidal surface portions adjoining and concentric with the marginal edges of each of said recesses for selective reception of and locking engagement with the toroidal surface on said locking means.

5. An orthopaedic walker as set forth in claim 4 wherein said locking means includes a stem portion protruding axially from said toroidal surface for selective entry into and initial alignment of said locking means relative to each of said recesses.

6. An orthopaedic walker as set forth in claim 1 wherein one of said hinge members on said one side of the patient's ankle includes thereon indicia of spaced angular relationships between said shoe and said leg support members and the other of said hinge members on said one side of the patient's ankle includes a portion overlying said indicia and having an indicator window therein for revealing said indicia one at a time in correspondence with the angular position of said shoe relative to said leg support members, thereby to facilitate selection of the locked position of angular adjustment of said shoe relative to said leg support members and to facilitate return of said shoe to such selected position following exercise.

7. An orthopaedic walker as set forth in claim 6 wherein said hinge members on both sides of the patient's ankle are of the same construction as one another and both include retention means and locking means as set forth in claim 1, and indicia and an indicator window as set forth in claim 6, whereby the members on both sides of the patient's ankle may be conveniently locked in, released from and quickly returned to the same position of angular adjustment.

8. An orthopaedic walker as set forth in claim 1 wherein the leg support member on said one side of the patient's ankle includes a portion extending upwardly and inwardly above the malleolus on said one side of the patient's ankle and having on the upper surface thereof indicia of spaced angular relationships between said shoe and said leg support member, and indicator means associated with said shoe on said one side of the patient's ankle for cooperation with said indicia for indicating the angular relationship between said shoe and said leg support member.

9. An orthopaedic walker as set forth in claim 8 wherein said first hinge member on said one side of the patient's ankle includes a portion inclined upwardly and inwardly over said upwardly and inwardly inclined portion of said leg support member and said indicia thereon, and said indicator means comprises a window in said upwardly and inwardly inclined portion of said first hinge member for selectively revealing said indicia in correspondence with the angular position of said shoe relative to said leg support member.

10. An orthopaedic walker as set forth in claim 1 wherein said locking means includes and is operable by a manually rotatable hand grip protruding outwardly from the walker at said one side of the patient's ankle, and the walker includes a protective cover having a releasable press fit over said hand grip and means for securing said cover to the walker for preventing rotation of said cover, said cover when pressed onto said hand grip mitigating against rotation of said hand grip and thereby mitigating against inadvertent tightening or loosening of said locking means.

11. An orthopaedic walker as set forth in claim 10 wherein said hand grip has a slot therein for reception of a tool for facilitating rotation and thereby tightening and loosening of said locking means, said cover includes a recess within the interior thereof for reception of such a tool, and a tool is removably mounted within said recess and includes a portion adapted to be inserted in said hand grip slot to facilitate rotation of said hand grip.

12. An orthopaedic appliance for an articulated joint of the body of a patient and the members of the patient's body joined by such joint, comprising a first support member for securement to a patient's body adjacent to and at one side of an articulated joint of the patient's body, a second support member for securement to the body member of the patient at the other side of the joint adjacent to the joint, a first hinge member on said first support member aligned with the articulated joint of the patient, a second hinge member on said second support member aligned with said first hinge member and the articulated joint of the patient, means connecting said first and second hinge members for oscillatory movement about an axis substantially coincident with the axis of articulation of the articulated joint of the patient, one of said hinge members including retention means in the form of an arc substantially concentric with the axis of oscillatory movement between said hinge members, locking means associated with and adjustably mounted on the other one of said hinge members in alignment with said retention means, said locking means including thereon at least one surface lockingly engageable with said retention means, said hinge members being angularly adjustable relative to one another, said locking means being adjustable to engage said surface thereon selectively with said retention means for releasably locking said hinge members together in any of a plurality of positions of relative angular adjustment of said hinge and support members, said locking means being adjustable to be disengaged from said retention means while remaining associated with said other hinge member to accommodate free floating oscillatory movement of said support members and articulation of the patient's joint, whereby said hinge and support members may be locked in any selected position of relative angular adjustment of said support members, quickly released from the selected position to accommodate rehabilitative articulation of the patient's joint, and quickly returned to and locked in the selected position of adjustment.

13. An orthopaedic appliance as set forth in claim 12 wherein said locking means includes a cam portion having a toroidal surface facing toward and engageable with juxtaposed surface portions of said retention means, and said juxtaposed surface portions of said retention means include arcuately spaced complementary toroidal surface portions for selective reception of and locking engagement with the toroidal surface on said locking means.

14. An orthopaedic appliance as set forth in claim 12 including first and second support members, first and second hinge members, retention means and locking means on both sides of the patient's joint aligned with the axis of articulation of the joint, corresponding ones of said first and second hinge members bearing indicia of the relative angular positions of relative adjustment of the respective support members, the other ones of said first and second hinge members each including portions overlying said indicia and having a window therein for revealing said indicia one at a time, whereby to facilitate adjustment of the hinge members on the opposite sides of the joint to the same angle.

15. An orthopaedic appliance for an articulated joint of the body of a patient and the members of the patient's body joined by such joint, comprising a first support member for securement to a patient's body adjacent to and at one side of an articulated joint of the patient's body, a second support member for securement to the body member of the patient at the other side of the joint adjacent to the joint, a first hinge member on said first support member aligned with the articulated joint of the patient, a second hinge member on said second support member aligned with said first hinge member and the articulated joint of the patient, means connecting said first and second hinge members for oscillatory movement about an axis substantially coincident with the axis of articulation of the articulated joint of the patient, an arcuate slot in one of said hinge members substantially concentric with the axis of oscillatory movement between said hinge members, locking means adjustably mounted on the other one of said hinge members in alignment with said slot, said locking means extending into said slot and including thereon at least one surface engageable with surface portions on said one hinge member adjoining the margins of said slot, said locking means being adjustable to engage said surface thereon selectively with said surface portions on said one hinge member for releasably locking said hinge members together in any one of a plurality of positions of relative angular adjustment of said support members, and to be disengaged from said surface portions on said one hinge member while remaining associated with said other hinge member to accommodate free floating movement of said support members and articulation of the patient's joint, whereby said hinge and support members may be locked in any selected position of relative angular adjustment of said support members within the limits of oscillatory movement accommodated by the arcuate extent of said slot, quickly released from the selected position to accommodate rehabilitative articulation of the patient's joint, and quickly returned to and locked in the selected position of adjustment.

16. An orthopaedic appliance as set forth in claim 15 wherein said arcuate slot comprises a plurality of angularly spaced notches and said surface of said locking means is selectively engageable with surface portions on said one hinge member adjoining the marginal edges of each of said notches for selectively locking said hinge members in any one of the angular positions defined by said notches.

17. An orthopaedic appliance as set forth in claim 16 wherein said locking means includes a cam portion having a toroidal surface facing toward and engageable with juxtaposed surface portions on said one hinge member, and said juxtaposed surface portions on said one hinge member include complementary toroidal surface portions adjoining and concentric with the marginal edges of each of said notches for selective reception of and locking engagement with the toroidal surface on said locking means.

18. An orthopaedic appliance as set forth in claim 17 wherein said locking means includes a stem portion protruding axially from said toroidal surface for selective entry into and initial alignment of said locking means relative to each of said notches.

19. An orthopaedic appliance as set forth in claim 15 wherein one of said first and second hinge members comprises a yoke including spaced, generally parallel first and second hinge plates and a bearing interposed between said first and second hinge plates, and the other of said first and second hinge members comprises a third hinge plate inserted between said first and second hinge plates and rotatably mounted on said bearing for oscillatory movement relative to said first and second hinge plates.

20. An orthopaedic appliance as set forth in claim 19 wherein said arcuate slot is formed in said third hinge plate substantially concentric with said bearing, and said locking means includes a threaded stud secured to one of said first and second hinge plates and extending into said slot, and a locking member threaded on said stud and extending through the other one of said first and second hinge plates for engagement with said third hinge plate.

21. An orthopaedic appliance as set forth in claim 20 wherein said locking member includes a cam portion concentric with said stud having thereon a toroidal surface facing toward and engageable with juxtaposed surfaces on said third hinge plate, and said arcuate slot comprises a plurality of angularly spaced notches in said third hinge plate and said juxtaposed surfaces on said third hinge plate include complementary toroidal surface portions adjoining and concentric with the marginal edges of each of said notches for selective reception of and locking engagement with the toroidal surface on said cam.

22. An orthopaedic appliance as set forth in claim 20 wherein said third hinge plate bears indicia of various positions of angular adjustment between said support members, and said other one of said first and second hinge plates overlies said indicia and has a window therein for revealing said indicia one at a time.

* * * * *

UNITED STATES PATENT AND TRADEMARK OFFICE
CERTIFICATE OF CORRECTION

PATENT NO. : 5,176,623    Page 1 of 2
DATED     : January 5, 1993
INVENTOR(S) : Joe G. Stetman and Adriaan C. Pruyssers It is certified that error appears in the above-identified patent and that said Letters Patent is hereby corrected as shown below:

On title page, item [54] and col 1, line 1

Change "OTHOPAEDIC" to --ORTHOPAEDIC--.

In the Abstract:

Line 15, change "the" to --in--.

Line 19, change "execise" to --exercise--.

Line 25, change "afrticulation" to --articulation--.

In the Claims:

Column 12, delete line 20, and insert in place thereof --a pair of first hinge members on the sidewall portions of--.

Column 12, delete line 37.

Column 12, line 58, delete "said", second occurrence, and replace with --a--.

Column 13, line 32, change "sad" to --said--.

UNITED STATES PATENT AND TRADEMARK OFFICE
CERTIFICATE OF CORRECTION

PATENT NO. : 5,176,623

DATED : January 5, 1993

INVENTOR(S) : Joe G. Stetman and Adriaan C. Pruyssers

It is certified that error appears in the above-indentified patent and that said Letters Patent is hereby corrected as shown below:

Column 16, lines 1-18, should appear as an uninterrupted continuation of the paragraph commencing in the penultimate line in column 15.

Signed and Sealed this

Sixteenth Day of November, 1993

Attest:

BRUCE LEHMAN

*Attesting Officer*  *Commissioner of Patents and Trademarks*